(12) United States Patent
Uchimiya et al.

(10) Patent No.: US 6,759,526 B2
(45) Date of Patent: Jul. 6, 2004

(54) DNA FRAGMENT HAVING PROMOTER FUNCTION

(75) Inventors: Hirofumi Uchimiya, Kawasaki (JP); Hiromitsu Fukuzawa, Saitama (JP); Michito Tagawa, Saitama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 12 days.

(21) Appl. No.: 10/148,689

(22) PCT Filed: Dec. 1, 2000

(86) PCT No.: PCT/JP00/08533

§ 371 (c)(1),
(2), (4) Date: May 31, 2002

(87) PCT Pub. No.: WO01/40470

PCT Pub. Date: Jun. 7, 2001

(65) Prior Publication Data

US 2003/0145344 A1 Jul. 31, 2003

(30) Foreign Application Priority Data

Dec. 2, 1999 (JP) ............................................ 11-343624

(51) Int. Cl.⁷ ........................ C07H 21/00; C07H 21/02; C12N 15/00; C12N 15/09; C12N 15/63
(52) U.S. Cl. ................... 536/23.1; 435/320.1; 435/419; 800/278
(58) Field of Search ...................... 536/23.1; 435/320.1, 435/419; 800/278

(56) References Cited

FOREIGN PATENT DOCUMENTS

JP 10-248570 9/1998

OTHER PUBLICATIONS

Yu L.H. et al., "Molecular Characterization of Methallothinonein Genes in Plants", Plant Biotechnol, vol. 15 (4), pp 167–172 (1998).

Wing R.A. et al., "A BAC End Sequencing Framework to Sequence the Rice Genome", Genbank, Acc. No. AQ257030 (Oct. 23, 1998).

Wing R.A. et al., "A BAC End Sequencing Framework to Sequence the Rice Genome", Genbank, Acc. No. AQ329061 (Jan. 8, 1999).

Wing R.A. et al., "A BAC End Sequencing Framework to Sequence the Rice Genome", Genbank, Acc. No. AQ854084 (Nov. 3, 1999).

Yu, Li–Hua et al., Gene 206 (1988) pp. 29–35.

Primary Examiner—Remy Yucel
Assistant Examiner—Konstantina Katcheves
(74) Attorney, Agent, or Firm—Birch, Stewart, Kolasch & Birch, LLP

(57) ABSTRACT

This invention provides a DNA fragment having a promoter function capable of expressing a structural gene which can be expressed in a plant, and discloses a DNA fragment having a promoter function in a plant which is originated from a gene encoding a rice metallothionein as shown by SEQ ID NO: 1, a vector comprising the DNA having the promoter function, a plant cell transformed by the vector; and a regenerated plant and seeds obtainable from the plant cells.

14 Claims, No Drawings

DNA FRAGMENT HAVING PROMOTER FUNCTION

This application is the national phase under 35 U.S.C. § 371 of PCT International Application No. PCT/JP00/08533 which has an International filing date of Dec. 1, 2000, which designated the United States of America.

TECHNICAL FIELD

This invention relates to a DNA fragment having a promoter activity in plants. More particularly, this invention relates to a novel DNA fragment having a promoter activity derived from a gene encoding metallothionein and a vector containing the same and a plant cell, a plant and a seed transformed thereby.

BACKGROUND ART

Improvement of plants by using a genetic engineering method has become practical recently. Particularly, a mechanism of tumor formation in plant by Ti plasmid of Agrobacterium tumefaciens which is a soil microorganism is solved in molecular level, and taking this opportunity, since a transformation system using a Ti plasmid vector has been established, research on plants in molecular level has been making a significant progress. In these days, the transformation system using the Ti plasmid vector can be applied to a main agricultural products including rice, soy been, etc., as well as to the model plants such as tobacco and *Arabidopsis thaliana*, etc.

It has been generally known that a 5' upstream region of a structural gene called promoter is involved in a transcription of a gene. The promoter is a DNA sequence located in an upstream region of a structural gene, containing a signal (TATA region) for an RNA polymerase to start transcription, thereby enabling a following protein synthesis. Therefore, the promoter is an important and essential gene to produce a genetically recombinant plant.

In a 5' upstream of the TATA region, there exists a specific nucleotide sequence called cis element, and this region interacts with a DNA binding protein (trans element) to determine a strength of promoter activity and control of the transcription.

For example, a promoter of *Arabidopsis thaliana* gene (rd29A) whose expression is induced by drought [Koizumi et al., Gene 129:175–182 (1993)] was isolated, and after that, from a research in which a promoter region is mutated by deletion or a research in which various kinds of DNA fragments are linked, it has been reported that the cis element of rd29A gene controlling an induction by drought is a 9 base sequence comprising TACCGACAT [Yamaguchi-Shinozaki et al., J. Plant Res. 108:127–136 (1995)], and it has been elucidated that the above mentioned cis element comprising 9 bases is essential for serving as a promoter induced by drought.

Currently, as a promoter for a gene transduction, 35S promoter of a cauliflower mosaic virus [Guilley et al., Cell 30:763–773 (1982)] has been frequently used. From analyses using tobacco [Morell et al., Nature 315:200–204 (1985)] on petunia [Sander, Nucl. Acid Res. 15:1543–1558 (1987)], 35S promoter has been shown to have an activity 30 times or more as strong as that of nopaline synthetase promoter. As shown above, since the promoter activity of 35S promoter is strong in dycotyledons, this promoter is widely used in order to transfer a structural gene and have it highly expressed in dicotyledons.

However, 35S promoter shows only relatively low promoter activity in a rice family plant which is an important monocotyledon in agriculture [Hauptmann et al., Plant Cell Rep. 6:265–270 (1987)].

On the contrary, a promoter derived from alcohol dehydrogenase (Adh) of corns merely gives an extremely low expression in protoplast of *Nicotiana plumbaginifolia* which is a dicotyledon [Ellis et al., EMBO J. 6:11–16 (1987)].

In order to produce practically useful novel plant strain in a wide range of plants by recombinant DNA technology in the future, it is thought to be an important technology, how to carry out efficiently an expression of a structural gene to be transferred or how to control an expression. However, with the 35S promoter or the Adh promoter, it is not easy to control a tissue-specific expression, or to control an expression by chemical substances.

Therefore, a promoter having a promoter activity not only in monocotyledons but also in dicotyledons, and being able to control a tissue specific and part specific expression has been sought.

Incidentally, metallothionein (Mt) has been known as a protein with a low molecular weight, playing an important role in metabolism of metals in vivo in animals, microorganisms and plants [Yu et al., Gene 206:29–35 (1998)].

Mt was initially isolated from the kidneys of horses and research on its structure and its function has made progress by using organisms such as cyanobacteria or fungi as a sample [Yu et al., Plant Biotechnology 15:167–172 (1998)]. When Mt originated from Chinese hamster is expressed in a metallo-sensitive yeast, the yeast becomes resistant to cadmium. This suggests Mt takes a part in detoxification of metals.

Regarding rice Mt gene, cDNA has been isolated from YAMAHOUSHI, and a promoter region has been isolated from Sasanishiki, whose base sequences have been reported [Japanese Provisional Patent Publication No. 10-248570].

The present invention has been aimed to obtain and provide a novel DNA fragment having a promoter activity which makes a linked exogenous structural gene express in the plant or plant cells, and enabling an induction of expression or control of a tissue-specific and part-specific expression by substances.

The present inventors have made intensive studies to solve the above-mentioned problems and they have isolated a promoter region of Mt gene from rice plant NNipponbare. As a result of comparison of nucleotide sequences with a promoter region isolated from Sasanishiki, the both sequences are totally different and a novel promoter has been identified. Further, they have found that this promoter has a promoter activity in a different plant strain, regardless of monocotyledons or dicotyledons, and that it enables an expression of an exogenous gene and control of the expression, and thus, the present invention has been completed.

SUMMARY OF THE INVENTION

The present invention comprises promoters shown below, which is derived from a gene encoding a rice metallothionein. That is, it is a DNA fragment having a promoter activity comprising a whole or a part of a base sequence shown by SEQ ID NO:1 wherein one or two or more bases maybe deleted, inserted or substituted provided that the sequence has a function in plants or in plant cells to control expression of a structural gene which can be expressed in plants, for example, a DNA of about 2.7 Kbp shown by SEQ ID NO:2.

Further, the present invention is an expression vector into which a DNA fragment shown by SEQ ID NO:1 or 2 is transferred.

In addition, the present invention relates to an expression vector wherein the DNA sequence shown by SEQ ID NO:1 or 2 is transferred to an exogenous structural gene.

Yet further, the present invention relates to a transformed plant cell obtainable by introducing the above-mentioned vector into a host plant cell, a transformed plant regenerated from the plant cells and a seed obtainable from the plant.

BEST MODE FOR CARRYING OUT THE INVENTION

In the description below, unless otherwise specified, recombinant DNA technology used as a conventional method can be carried out using techniques described in the following reference: "Molecular Cloning" (Fristch et al., Cold Spring Harbour Press (1989)).

The DNA fragment having a promoter activity of the present invention can be isolated from a plant genomic library by a plaque hybridization, etc. using cDNA of rice metallothionein as a probe.

Genomic library can be obtained by extracting genomic DNA from plant such as a rice plant, partially digesting the isolated genomic DNA by an appropriate restriction enzyme such as EcoRI, fractionating longer DNA fragments, for example, DNA fragments of 9 to 23 kb by sucrose density-gradient centrifugation or by agarose gel electrophoresis, incorporating this into an appropriate vector such as λ phage and packaging, followed by infecting Escherichia coli such as XL-1 Blue strain with this recombinant phage, and culturing them on a flat culture medium such as an LB plate (1% Bactotryptone, 0.5% yeast-extract, 1% NaCl and 1.3% agarose). As a vector, a plasmid may be used, however, it is preferable to use λ phage or cosmid vector in that longer DNA fragments can be effectively inserted.

Membrane such as nylon membrane is placed on the above-mentioned flat culture medium, and this membrane is immersed in a denaturing agent, followed by immersing in a neutralizing solution and washing with a washing solution, so that the recombinant DNAs on the flat culture medium become single stranded and are adsorbed onto the membrane.

As a probe, for example, an oligo DNA synthesized according to a part of Mt structural gene or a DNA amplified by the PCR method using Mt cDNA is labeled with [α-$^{32}$P] dCTP, DIG (Digoxigenin), biotin, etc. and used.

Hybridization can be carried out using the membrane to which the above-mentioned single stranded DNAs are adsorbed and the labeled probe.

The membrane thus hybridized with the labeled probe is applied to autoradiography to detect clones strongly hybridized with the probes, and they can be isolated as positive clones.

DNA of the isolated positive clone is treated with an appropriate restriction enzyme, such as Eco RI, carrying out subcloning with an appropriate cloning vector such as pBluescript II and pUC type vector, and then, its nucleotide sequence can be determined by the Maxam-Gilbert method or by dideoxy method, etc. Commercially available kits, and an automated sequencer that automatically determines a sequence, etc. may be used.

Base sequence of the obtained clone is determined as mentioned above and the 5' non-translated region and its upstream promoter region of the Mt gene are found out.

To a downstream of the thus obtained promoter region, a structural gene and a terminator gene are linked, and by inserting them into an expression vector, it is possible to construct an expression vector for gene transfer.

As an expression vector, there may be mentioned pUC type vector (for example, pUC118, pUC119), pBR type vector (for example, pBR322), pBItype vector (for example, pBI101, pBI112 and pBI221), pGA type vector (pGA492 and pGAH), etc. In addition to these, virus vectors, etc. may be listed.

As a terminator gene to be linked, there may be mentioned 35S terminator gene, Nos terminator gene, etc.

As a structural gene to be linked, there may be mentioned, for example, a reporter gene, a gene of an insecticidal protein, a herbicide-resistant gene, a gene expressing antibacterial activity, blight resistant gene, a gene which induces bloom of plants, a gene involving morphogenesis, a gene involving resistance to an environmental stress, a gene involving in increasing an yield, a gene with an antiseptic effect on crops, etc.

As a reporter gene, there may be mentioned β-glucuronidase (GUS) gene, luciferase gene, chloramphenicol acetyltransferase (CAT) gene, etc. As a gene of an insecticidal protein, there may be mentioned a gene of a crystalline protein of Bacillus thuringiensis, a protease inhibitor gene, etc., as a herbicide-resistant gene, a gliphosate-resistant gene, a glufosinate-resistant gene, a sulfonylurea type herbicide resistant gene, etc., as a gene expressing antibacterial activity, chitinase gene, glucanase gene, lysozyme gene, cecropin gene, etc., as a gene which induces bloom of plants, a gene involving formation of florigen, etc., as a gene involving morphogenesis, chalcone synthase gene, phenylalanine ammonia-lyase, RolC gene, etc., as a gene involving resistance to an environmental stress, glutamine synthase gene, glycine betaine gene, Mt gene, etc., as a gene involving in increasing a yield, a modified gene of a seed storage protein, sucrose-phosphate synthase gene, etc., and as a gene with an antiseptic effect on crops, an antisense gene of ethylene synthase gene, etc.

As a method for introducing an expression vector in which a structural gene such as a reporter gene and a terminator gene are linked to a downstream of a promoter, there maybe mentioned an indirect introducing method or a direct introducing method.

As the indirect introducing method, for example, a method using Agrobacterium is exemplified.

As the direct introducing method, there may be exemplified, for example, an electroporation method, a particle gun method, a polyethylene glycol method, a microinjection method, a silicon carbide method, etc.

All kinds of plants are included as a plant to which a gene is transferred, and, for example, there may be mentioned the rice family, the palm family, the lily family, the orchid family, the taro family, etc., for monocotyledon plants.

Examples of the rice family may include a rice plant, wheat, barley, ryewheat, brushwood, a ditchreed, asugarcane, corn, foxtail millet, a barnyard grass, etc. Examples of lily family may include a Welsh onion, a lily, a tulip, etc.

For dicotyledon plants, examples may include the beech family, the cactus family, the camellia family, the mallow family, the gourd family, the rape family, the rose family, the pulse family, the mulberry family, Euphorbia family, the grape family, the tangerine family, the drop wort family, the eggplant family, the perilla family, the crysanthemum family, the primrose family, the fringed pink family, etc. As the camellia family, tea, etc. are mentioned. As the mallow family, cotton, etc. are mentioned. As the gourd family, cucumber, melon, pumpkin, etc. are mentioned. As the rape family, rape, Arabidopsis thaliana, Japanese radish, horseradish, cabbage, etc. are mentioned. As the rose family, Japanese apricot, peach, apple, pears, rose, etc. are mentioned. As the pulse family, soybean, adzuki bean, garden pea, broad bean, peanut, etc. are mentioned. As the mulberry family, hop, etc. are mentioned. As the eggplant family, tobacco, eggplant, potato, tomato, etc. are mentioned. As the crysanthemum family, crysanthemum, garden crysanthemum, sunflower, lettuce, etc. are mentioned. As the primrose family, primrose, cyclamen, etc. are mentioned. As the fringed pink family, carnation, etc. are mentioned.

Further, plants which belong to a gymnosperm, such as Japanese cedar family, pine tree family, white cedar family, etc. are also included.

A plant which contains the transferred promoter and the structural gene can be obtained by inserting a gene having a resistance to chemicals such as kanamycin, hygromycin, etc. to a gene transferred vector, or by simultaneously introducing a vector having a chemical resistant gene to a plant, and then, selecting with a chemical such as kanamycin or hygromycin, etc. Further, by analyzing the gene transferred into the plant, such as a PCR method or a southern hybridization method, etc., or by analyzing a translated product of the transferred structural gene, for example, by analyzing a desired protein contained in an extract of the plant leaves, etc. in terms of enzyme activity or by a Western blotting method, etc., thereby confirming and selecting plants to which the desired gene is transferred.

It is possible to grow the thus obtained transformed plant to collect its seeds, and to differentiate and regenerate a plant using a tissue of the transformed plant, such as a leaf or a root.

Since Mt gene is localized in the internode, it is possible to control site of expression of the transferred gene in the transformed plant into which it is transferred, by linking a structural gene to a downstream of the promoter region.

Analysis on site-specific expression of the structural gene which is linked and transferred into the promoter is carried out by analyzing localization of mRNA or a translated product of the structural gene in the plant.

For example, when a GUS gene is used as a structural gene, an existing site of GUS in the transformed plant can be confirmed by a histochemical method.

That is, localized site of GUS can be confirmed by observing tissue by a microscope for a blue color of indigotin, that is a hydrolysis product of 5-bromo-4-chloro-3-indolyl-β-D-glucuronic acid by GUS.

EXAMPLES

In the following, Examples of the present invention will be explained more specifically, but, the present invention is not limited by these.

Example 1

Preparation of Rice Genomic Library

For preparing a rice genomic library, genomic DNA was extracted and isolated from leaves of rice plant 2 weeks after seedling (strain: NNipponbare). Isolated genomic DNA was partially digested by Mbo I. The reaction mixture was extracted with phenol-chloroform, the obtained aqueous layer was precipitated with ethanol, and then, the resultant precipitate was dissolved in a TE buffer to obtain Mbo I fragments of genomic DNA.

The thus obtained Mbo I fragments of the genomic DNA were cloned using λ-GEM12Xho I Half-site Arms Cloning System (manufactured by Promega Co.). That is, the Mbo I fragments of the genomic DNA were inserted into Xho I sites of the phage vector λ-GEM12, and packaged in phage particles, and then, this recombinant phages were plated on an NZYM (1% NZ amine, 0.5% Yeast Extract, 0.5% NaCl, 0.2% $MgSO_4 \cdot 7H_2O$ and 1.3% agarose) plate together with a top agar containing Escherichia coli (KW 251), followed by overnight culture at 37° C. to form plaques.

Example 2

Screening of Rice Genomic Library (a) Preparation of Membrane

After the above-mentioned NZYM plate with formed plaques were refrigeratea, a membrane (Hydona $N^+$, manufactured by Amersham Co.) marked with a pencil was placed thereon, left for 2 minutes, and then, it was marked by stabbing through it and into the agar with a needle, and removed. This membrane was impregnated into a solution of 1.5M NaCl and 0.5M of NaOH for 2 minutes for denature and neutralized by impregnating it into a solution of 1.5M Tris-HCl (pH 7.5) and 2×SSC for 5 minutes. Subsequently, the membrane was immersed in a solution of 0.2M Tris-HCl (pH 7.5) and 2×SSC for 30 seconds to wash it, and dried on a filter, so that recombinant DNA on the NZYM plate was adsorbed on the membrane as a single stranded state.

(b) Preparation of Probe

A probe was prepared according to a method as mentioned below, using cDNA of Mt isolated by Yu et al. [Yu et al., Gene 206:29–35 (1998)] and using Random Primer DNA Labeling Kit Ver.2.0 (manufactured by Takara Co.) for labeling DNA. Into a tube were charged 1 μg of Mt cDNA and 2 μl of Random Primer, and the total volume was made 14 μl with a sterilized water. To the mixture were added each 2.5 μl of 10× buffer and dNTP mixture and 5 μl of [α-$^{32}$P] dCTP (1.85MBq). 1 μl of Exo-free Klenow Fragment was added and kept at 37° C. for 10 minutes, followed by heating at 65° C. for 5 minutes to obtain a probe.

(c) Hybridization

The membrane to which the above-mentioned single stranded DNA was attached was placed in a Hybri-Bag, a hybridization buffer (5×SSC, 5×Denhardt's reagent, 0.5% SDS) was added in an amount of 5 ml per 100 $cm^2$ of the membrane, and salmon sperms DNA that had been treated with ultrasonic wave, heated and quenched were added to make its concentration 0.1 mg/ml, and then, the mixture was incubated at 65° C. for 1 hour. The above-mentioned labeled probe was heated and quenched, and it was added to the above mixture in a corresponding amount of $10^5$–$10^6$ cpm per 1 ml of the hybridization buffer. After sealing it, hybridization was carried out at 65° C. overnight. Subsequently, the membrane after completion of hybridization was washed by shaking in a washing solution A (0.1% SDS, 2×SSC) at a room temperature for 10 minutes, and then, washed by shaking in a washing solution B (0.1% SDS, 1×SSC) at 65° C. for 30 minutes. Repeatedly, in a fresh washing solution B, it was washed by shaking at 65° C. for 30 minutes, and air-dried.

(d) Autoradiography

After the air-dried membrane was wrapped with a plastic film, it was subjected to autoradiography to obtain an autoradiography film. By adjusting the mark left on the membrane and the mark left on the agar plate, phages that were strongly hybridized with the probe were detected by the positions of positive signals on the film, and they were isolated as positive phages. Among about million phages, 7 positive phages were obtained.

Example 3

Determination of Nucleotide Sequence (a) Preparation of DNA from Positive Phages From the isolated positive phages, DNA was isolated according to the method as mentioned below. Single phage was pickedup and suspended in 100 µl of an SM buffer solution (0.58% NaCl, 0.2% MgSO$_4$.H$_2$O, 0.01% gelatin and 0.05% Tris-HCl), and left alone at room temperature for 1 hour. To the solution was added *E.coli* (KW251) in an amount of 20 µl, and the mixture was left alone at 37° C. for 15 minutes. Subsequently, 5 ml of an NZYM medium was added thereto and followed by culture at 37° C. overnight. After the culture, 100 µl of chloroform was added to the culture liquid and subjected to shaking culture for 15 minutes. After centrifugal separation, to the obtained supernatant that is a phage containing liquid, RNase A and DNase I were added so that each concentration thereof became 5 µg/ml, and then, the mixture was incubated at 37° C. for 30 minutes. To the mixture was added an equivalent amount of 20% PEG6000-2.5M NaCl solution, and it was left still for 1 hour on ice. The obtained precipitate was suspended in 500 µl of an SM buffer solution. To the suspended solution were added EDTA (final concentration of 10 mM) and SDS (final concentration of 0.1%), and it was kept at 65° C. for 15 minutes, followed by extraction with phenol, extraction with phenol-chloroform, and extraction with chloroform, to obtain an aqueous layer. To the obtained aqueous layer was added an equivalent amount of isopropanol and left still at 80° C. for 10 minutes, followed by centrifugation. To the precipitate was added 70% ethanol and it was subjected to another centrifugation. The precipitate was dissolved in 50 µl of a TE buffer solution to obtain a phage DNA solution.

(b) Determination of Nucleotide Sequence of the Positive Phage DNA

Each of the thus obtained phage DNA was treated with several kinds of restriction enzymes including Eco RI, and separated by means of agarose gel electrophoresis, followed by the Southern blotting analysis using a whole Mt cDNA as a probe. From the results, an Eco RI DNA fragment (about 4 Kbp) that was thought to contain a region identical to the Mt cDNA was recovered from the agarose gel, using a centrifugation tube equipped with a filter for DNA recovery (SUPREC-01, manufactured by TaKaRa Co.). The recovered DNA fragments were ligated to a restriction enzyme site (Eco RI) of pBluescript II (manufactured by STRATAGENE Co.), using a DNA ligation kit (Ligation Kit) (manufactured by TaKaRa Co.), and transferred into *E.coli* (XL1-Blue). The thus obtained clone was named pMt (Eco RI), and its nucleotide sequence was determined according to the dideoxy method, using a sequencing kit for determining nucleotide sequence (Sequencing High -Cycle-, manufactured by TOYOBO Co.). Further, nucleotide sequences of a plural number of deletion mutant clones with different lengths of deletion parts, prepared from the obtained clones using a Deletion Kit for Kilo-Sequence (manufactured by TaKaRa Co.) was determined, according to the dideoxy method, using a sequencing kit for determining nucleotide sequence (Sequencing High -Cycle-, manufactured by TOYOBO Co.).

(c) Analysis on Determined Nucleotide Sequence

The thus determined nucleotide sequence of the clone was analyzed by using a genetic information analyzing software (GENETYX-MAC Ver.8, manufactured by Software Kaihatsu K.K.), to determine a nucleotide sequence of about 4.0 Kb as shown in SEQ ID NO:3. Further, it was found that a translation start codon (ATG) clarified by analysis of Mt cDNA existed in nucleotide sequence No. 3055–3057 of SEQ ID NO:3 in the Sequence Listing.

From a promoter analysis using a genetic information analyzing software (GENETYX-MAC Ver.8, manufactured by Software Kaihatsu K.K.), TATAbox-like sequence was identified in nucleotide sequence No. 2928–2935 (8 bases) of SEQ ID NO:3.

Example 4

Detection of Promoter Activity (a) Gene Transfer into Plant

Three kinds of primers were synthesized based on the nucleotide sequence determined in Example 3, and PCR was carried out. PCR product obtained by using a primer shown in SEQ ID NO: 4 and a primer shown in SEQ ID NO: 5 was named Mt pro1, and PCR product obtained by using a primer shown in SEQ ID NO: 4 and a primer shown in SEQ ID NO: 6 was named Mt pro2, respectively. Each of them were separated by an agarose gel electrophoresis, and then, DNA fragments about 2.8 Kbp and about 2.7 Kbp were recovered from the agarose gel, using a centrifugation tube equipped with a filter for DNA recovery (SUPREC-01, manufactured by TaKaRa Co.). The obtained DNA fragments were inserted into a Sal I and Bam HI sites of a gene transferred vector for a plant having kanamycin and hygromycin resistant genes and GUS gene (a vector pNC obtained by introducing a hygromycin resistant gene into pBI101 for), which enables confirmation of a gene transferred into aplant. These vectors were named pNC/Mt pro1-GUS and pNC/Mt pro2-GUS, respectively. According to the method described below, these two kinds of gene-transferred vectors were transferred into an Agrobacterium (LBA4404 strain and EHA101).

The Agrobacterium was cultured using a YEP liquid culture medium (1% Bacto-peptone, 1% Bacto-yeast extract and 0.5% NaCl), until its absorbance at 600 nm at 28° C. reached around 1.0. After the culture liquid was chilled on ice, it was subjected to centrifugation. The precipitated cells were suspended in 1 ml of 20 mM CaCl$_2$ solution, and frozen by liquid nitrogen. 1 µg of DNA of either pNC/Mt pro1-GUS or pNC/Mt pro2-GUS was added and the mixture was thawed at 37° C. for 5 minutes. 1 ml of a YEP liquid culture medium was added thereto, and the resulting material was subjected to a shaking culture gently at 28° C. for4 hours. The culture liquid was centrifuged and the precipitated cells were suspended in 0.1 ml of a YEP liquid culture medium and plated onto a YEP plate (containing 1.5% agarose, 50 µg/ml of kanamycin, 50 µg/ml of hygromycin), and it was cultured at 28° C. for 3 days to obtain a transformed Agrobacterium.

According to the method below, gene transferred into a tobacco plant was carried out.

First, the above transformed Agrobacterium was cultured at 28° C. overnight, using an LB liquid culture medium. Subsequently, leaves of tobacco plant grown under sterilized condition were cut into dices of 1 cm square, and immersed in the culture liquid of the above transformed Agrobacterium for 5 minutes for infection. After infection, the tobacco leaves from which excessive culture liquid was removed on a sterilized filter paper were placed on an MS-NB plate, and cultured under the light of about 3000 lux. Three days later, they were transferred to an MS-NB plate containing 500 µg/ml of chlaforan and cultured to remove the transformed Agrobacterium. Seven days later, they were transferred to an MS-NB plate containing 100 µg/ml of kanamycin and 500 µg/ml of chlaforan and cultured to obtain kanamycin-resistant individuals. Ten days later, when kanamycin-resistant differentiated foliages grew big, they were transferred to an MS plate without containing hormones and grew to give a transformed tobacco.

According to the method below, gene transferred into a rice plant was carried out.

The transformed Agrobacterium was cultured for 3 days under dark condition at 28° C., using an AB agar culture medium. Subsequently, calluses derived from a rice plant (NNipponbare) were immersed for 2 minutes in a suspension obtained by suspending the above transformed Agrobacterium into an AAM liquid culture medium containing 10 mg/l of acetosyringone, so that the calluses were infected. After infection, excess culture liquid was removed from the calluses on a sterilized filter paper, and then, the resulting calluses were placed on a 2N6 plate containing 10 mg/l of acetosyringone with a covering filter paper. They were cultured at 25° C. under dark condition. Three days later, sterilizing treatment was carried out to remove the transformed Agrobacterium, and the calluses were transferred to a N6D plate containing 500 mg/l of carbenicillin, and cultured at 25° C. under light of about 3000 lux After 14 days, they were transferred to a N6D plate containing 500 mg/l of carbenicillin, and 50 mg/l of hygromycin and cultured, to obtain hygromycin-resistant individuals. A few weeks later, they were transferred to an MSNK plate containing 500 mg/l of carbenicillin, and 50 mg/l of hygromycin to promote re-differentiation. When the hygromycin-resistant calluses were re-differentiated to give a shoot, they were then transferred to an MS plate without containing hormones, and let them grow to give transformed rice plants.

(b) Confirmation of Transferred Gene

Existence of transferred gene in the thus obtained transformed tobacco or rice plant was confirmed according to the CTAB method, using a genomic DNA extracted from the transformed tobacco as a template, amplifying the part between the promoter gene and the GUS gene by the PCR reaction using primers as shown by SEQ ID NO:4 and SEQ ID NO:7, followed by an agarose gel electrophoresis.

Composition of the reaction solution used in the PCR reaction was described below. As a heat-resistant DNA polymerase, Ampli Taq Gold (manufactured by Perkin Elmer Co.) was used.

| | |
|---|---|
| Extracted genomic DNA solution | 0.5 µl |
| 10XPCR buffer | 5.0 µl |
| 25 mM MgCl$_2$ | 4.0 µl |
| 2 mM dNPT mix | 5.0 µl |
| Heat-resistant DNA polymerase | 0.2 µl |
| 25 pmol/µl primer | 1.0 µl each |
| SDW | 33.3 µl |
| Total | 50.0 µl |

Conditions for the PCR reaction were as follows.

95° C. for 12 minutes;

40 cycles of 96° C. for 30 seconds, 55° C. for 1 minute and

72° C. for 4 minutes; and

72° C. for 10 minutes.

The PCR reaction solution was subjected to 1% agarose gel electrophoresis for separation. As a result, a DNA band with an objective size was detected, confirming the existence of the transferred Mt promoter region and GUS gene in both the Mt-GUS tobacco and rice plants.

(c) Measurement of Promoter Activity

Promoter activity was confirmed, according to the method below, by measuring an enzyme activity of GUS (GUS activity), that is a translated product of a reporter gene linked downstream of the promoter.

(c-1) Fluorometric Assay

About 100 mg of a section of a leaf or a root of the transformed plant was put into a microtube (1.5 ml) and 100 µl of an extraction buffer solution (50 mM phosphate buffer (pH 7.0), 10 mM EDTA, 0.1% Triton X-100, 0.1% N-Lauroyl-sarcosine Sodium Salt, 1 mM β-mercaptoethanol) was added thereto. The mixture was completely ground on ice, and subjected to a centrifugal separation to obtain about 100 µl of a supernatant. Using the obtained supernatant, measurement on a GUS activity and determination of an amount of the protein were carried out. With respect to a non-recombinant plant, measurement on a GUS activity and determination of an amount of the protein were carried out in the same manner, in measurement on the GUS activity, 170 µl of a buffer solution was added to 80 µl of the above-mentioned supernatant to give an extract solution. To the extract solution was added 250 µl of 4-methyl-umbelliferyl-β-D-glucuronide (4MUG) solution (1 mM 4MUG/extract buffer solution) as a substrate, and a reaction was started at 37° C. A part (100 µl) of the reaction liquid was portioned after 10 minutes or 40 minutes after the start of the reaction, and added to 2 ml of a reaction-terminating solution (0.2 M sodium carbonate) to terminate the reaction. As a blank, a mixture wherein only 100 µl of an extract solution was added to 2 ml of a reaction-terminating solution was used, and as a control, a mixture wherein 50 µl or 100 µl of 1 µM 4-methyl-umbelliferron (4MU) solution was added to 2 ml of a reaction-terminating solution was used. Fluorescences of these solutions were measured by using a fluorescence spectrophotometer (excitation wavelength=365 nm, emission wavelength=455 nm).

Determination of an amount of the protein was carried out according to the Bradford method, using a Bio-Rad Protein Assay Kit (manufactured by BIO-RAD Co.).

Based on the thus obtained numerical values, amounts of 4MU produced per unit time and unit amount of the protein were calculated. The GUS activity values were about 114 times and about 72 times, respectively, as that of non-recombinant plant, in Mt pro1-GUS tobacco and Mt pro2-GUS tobacco.

(c-2) Histochemical Assay

Plant tissue such as leaf, stem or root was cut off and immersed in a fixation solution (0.3% formamide, 10 mM MES and 0.3M mannitol), suctioned by a vacuum pump, and treated at room temperature for about 1 hour. Subsequently, the tissue was washed with a buffer solution (50 mM sodium phosphate, pH 7.0), and immersed in a 5-bromo-4-chloro-3-indolyl-β-D-glucuronic acid (X-Gluc) solution, and suctioned by a vacuum pump, and treated for 2 hours or more at 37° C. As a result, in both Mt-GUS tobacco and rice plants, blue color due to indigotin formation was expressed, confirming that the DNA fragments as shown in SEQ ID NO:1 and SEQ ID NO:2 had a promoter activity.

(c-3) Analysis on Plant of the Next Generation of Recombination by Histochemical Assay Seeds were collected from Mt pro1-GUS tobacco, Mt pro2-GUS tobacco, Mt pro1-GUS rice plant and Mt pro2-GUS rice plant that exhibited the GUS activity in the recombinant generation. By seedling these seeds, a plant of the next generation of recombination was obtained. Results from the tests of tissue staining by the histochemical assay showed expression of blue color due to indigotin formation in both Mt-GUS tobacco and rice plants. From these results, it was confirmed that the Mt promoter had a function also in the next generation of the recombination.

(c-4) Analysis on Plant of the Next Generation of Recombination by Fluorometric Assay Young seedling of Mt pro1-GUS tobacco obtained by seedling the seeds was dissected in respective tissues including leaf, stem and root, and analyzed by the fluorometric assay. As a result, Mt pro1 showed a GUS activity which corresponds to 35S promoter, all in leaf, stem and root. Similarly, young seedling of Mt pro1-GUS rice plant was dissected in respective tissues including leaf sheath, root and endosperm, and analyzed by the fluorometric assay. As a result, Mt pro1 showed a GUS activity which corresponds to 35S promoter in leaf sheath and root. On the other hand, there was no GUS activity detected in endosperm.

Industrial Applicability

The promoter of the present invention, that is linked to a useful gene and transferred in a plant or in a plant cell, enables an expression of the useful gene. In addition, since the promoter of the present invention is a promoter of Mt gene which is induced by heavy metals, virus infection or damage, it is possible to use it as a promoter to induce an expression of the transferred useful gene by an environmental stress. Moreover, since Mt is localized in internodes, it is possible to limit a tissue or a part where the transferred gene is expressed.

SEQUENCE LISTING

<160> NUMBER OF SEQ ID NOS: 7

<210> SEQ ID NO 1
<211> LENGTH: 2784
<212> TYPE: DNA
<213> ORGANISM: Oryza sativa L.cv.Nipponbare

<400> SEQUENCE: 1

| | | | | | |
|---|---|---|---|---|---|
| gtcgaccttc | gagtgccttc | acagaggtct | caactttact | tcatctgctg | catatataat | 60 |
| ttccctatca | tcgtgttcat | ttctctctca | tccaaaaggg | acaaagacac | accagagaca | 120 |
| acatgaatct | ctcctgtggc | catcatttct | acccaccata | tttgttttta | atgttgtcac | 180 |
| tctccttctc | tattaataca | taagctttta | cccctttca | aatatataat | tcacccactg | 240 |
| aataatgcac | tttcagagtt | agtgctccat | gctattttga | cttttgacct | gtttctttct | 300 |
| gcagggacg | tctcaaagca | caaagttgag | agtgcagtaa | gtatatataa | atacactcac | 360 |
| atttccatag | ctttgcatcc | gttattccat | tttctctcta | tctgctgttc | catcaaggac | 420 |
| agtttcttca | gaaatgaagt | tactgtttcc | ccacctaata | ctgctatact | cctgctgatc | 480 |
| ttgcgctcct | gaatttatat | gtatgcagct | caagaaaatt | tgcaaggaag | gcgcatattg | 540 |
| gggtataatt | aaataatcaa | ctcatctgca | tatataatct | cctacttcct | ccgtttcaca | 600 |
| atgtaagact | ttttagcatt | gcccatattc | atttagatgt | taatgaatct | agacatatgt | 660 |
| atgtgtttag | attcattaac | gtctatatgt | atatgagcaa | tgctagaaag | tcttacattg | 720 |
| tgaaacggag | ggagtacttg | attttctatt | aactcagctt | tgctcaaaac | taacaaaata | 780 |
| ctactgtcaa | cgtactcaag | cgcatgtgtt | gtatttttgt | taatctaaca | atggaagaaa | 840 |
| cacatattca | ggtgctattg | cgggtgtata | tgtgggcatg | gagtatggaa | tcgaaagaat | 900 |
| ccgtggtcac | agggactagg | taatatacgc | atatggtgtt | tgattaattt | ggtcggagta | 960 |
| aatctcaaaa | tacttggacc | aaactatcgc | aaagctacaa | atttaatgtt | gtgcatcaca | 1020 |
| aaactataaa | tttaatgact | tgtaccacga | aactacagat | tttgtaatga | atttatcaaa | 1080 |
| gaactacaga | ttttaaagtt | taaatcaata | gcctgttgtt | tttctgaaag | ttacaaaagc | 1140 |
| tacagtttta | taataaaatt | gatgttaaat | ttgtagtttg | gtgataattt | agtactaaat | 1200 |
| ctggcagacg | cactcttaaa | tatatagttt | tgtgatagtt | tgattaaagc | atctgtagtt | 1260 |
| ttggaaaatg | tactcatctg | ttcatgaata | tatactggct | gctgtctgtg | cagtgtgcac | 1320 |
| gatcgatctg | gatgttaact | tgcatttcct | tgggatgtgt | gtgtatgcaa | ttgagcagaa | 1380 |
| gaacgcgatg | gttggaggcg | ccgtaacagg | agcactggtg | tctgcggcga | gcaacagcca | 1440 |
| caggcagaac | gtggtgaaga | acgccatcac | tgggggagcc | atcgcaaccg | ctgcagagtt | 1500 |

```
cctcaattac cttacctgaa gtctgcatac tacttgttgt tgatctgtgc ccccaagaag    1560
aataacactc tactcttact tgttggaaaa aaatagtatt agcaaccacg catatgcaaa    1620
ttttaatgca gtaataataa agatggatc gatcgttttc cagctcttgt atatgtgact    1680
ggccctgctt tatgtgtgta gtgttaattt cagctttagc agtacgtgat tagtgatgga    1740
caataattgt cgcagacgta tctatcaatt gctcctgttg tgtgatgctt taactgttgg    1800
aatcaaagtt gcgttgcctt tgttgttatg aggaggagta tatatgttgg ggcaggaaaa    1860
gaatggagga gagatcgttc tccatatcct tatcatcggc ctcgtcactg ctcgcagttt    1920 aacttttgg tgatgcgggc gatggtcagc catatatata ctcccatgct gcatgctagt    1980
aatcaatata cgccttgtaa aagtaaacga tcgtctagta attgcaatat cataggggta    2040
gccattgaca gagatctaca tagatagagg gggaacaaga attgacactc cacagatgct    2100
ccactcattc acctttacta atttatatct tttgatgttt gatcgatcga tcgatccgtc    2160
cgtcggtgtc tcgacgaata aaaactgcaa atcgaactgt atgtatataa tatagcgtcg    2220
taaattaaat taaattaaat cgaactgaat actacatgtc gaagcaagaa ttagttcaac    2280
taaaagattt agttttccg gttgcaatat ttgtgaaatt aattgaagaa attaagaaga    2340
aaactggaga gatatatata tggatgagac aaaatgagat aagacgcatg gtggtccctc    2400
ggatgatgtt gtccgttcct tatttccatt ccatggcagc tgctatcgct atctagtgcg    2460
cgcggcatct ccaatcccat ccattctagt ggtcgatcta gctactactg agtattgttt    2520
tttcttcttt ttactactgt tgattattct gcaactgcag ttagatgctt gctactccta    2580
catcgatctc tctcgcgcgg gcgtatgcat tgcattcact actgatgatc cgtgggtgta    2640
gtgtgggtgg ctataaatag ggcagggtgc ggttgccatt gctcctcagg ccagcaactg    2700
agaagctcca tacaagtaag cagcagctag ttgccgacaa ggccagagaa ggaagaagaa    2760
gctctcatca tcatcaccgg atcc                                          2784

<210> SEQ ID NO 2
<211> LENGTH: 2699
<212> TYPE: DNA
<213> ORGANISM: Oryza sativa L.cv.Nipponbare

<400> SEQUENCE: 2
gtcgaccttc gagtgccttc acagaggtct caactttact tcatctgctg catatataat     60
ttccctatca tcgtgttcat ttctctctca tccaaaaggg acaaagacac accagagaca    120
acatgaatct ctcctgtggc catcatttct acccaccata tttgttttta atgttgtcac    180
tctccttctc tattaataca taagctttta cccctttca aatatataat tcacccactg    240
aataatgcac tttcagagtt agtgctccat gctattttga cttttgacct gtttctttct    300 gcagggacg tctcaaagca caaagttgag agtgcagtaa gtatatataa atacactcac    360
atttccatag ctttgcatcc gttattccat tttctctcta tctgctgttc catcaaggac    420
agtttcttca gaaatgaagt tactgttccc ccacctaata ctgctatact cctgctgatc    480
ttgcgctcct gaatttatat gtatgcagct caagaaaatt tgcaaggaag cgcatattg     540 gggtataatt aaataatcaa ctcatctgca tataatct cctacttcct ccgtttcaca    600
atgtaagact ttttagcatt gcccatattc atttagatgt taatgaatct agacatatgt    660
atgtgtttag attcattaac gtctatatgt atatgagcaa tgctagaaag tcttacattg    720
tgaaacggag gggagtacttg attttctatt aactcagctt tgctcaaaac taacaaaata    780
ctactgtcaa cgtactcaag cgcatgtgtt gtattttgt taatctaaca atggaagaaa    840
```

-continued

| | |
|---|---|
| cacatattca ggtactattg cgggtgtata tgtgggcatg gagtatggaa tcgaaagaat | 900 |
| ccgtggtcac agggactagg taatatacgc atatggtgtt tgattaattt ggtcggagta | 960 |
| aatctcaaaa tacttggacc aaactatcgc aaagctacaa atttaatgtt gtgcatcaca | 1020 |
| aaactataaa tttaatgact tgtaccacga aactacagat tttgtaatga atttatcaaa | 1080 |
| gaactacaga ttttaaagtt taaatcaata gcctgttgtt tttctgaaag ttacaaaagc | 1140 |
| tacagtttta taataaaatt gatgttaaat ttgtagtttg gtgataattt agtactaaat | 1200 |
| ctggcagacg cactcttaaa tatatagttt tgtgatagtt tgattaaagc atctgtagtt | 1260 |
| ttggaaaatg tactcatctg ttcatgaata tatactggct gctgtctgtg cagtgtgcac | 1320 |
| gatcgatctg gatgttaact tgcatttcct tgggatgtgt gtgtatgcaa ttgagcagaa | 1380 |
| gaacgcgatg gttggaggcg ccgtaacagg agcactggtg tctgcggcga gcaacagcca | 1440 |
| caggcagaac gtggtgaaga acgccatcac tgggggagcc atcgcaaccg ctgcagagtt | 1500 |
| cctcaattac cttacctgaa gtctgcatac tacttgttgt tgatctgtgc ccccaagaag | 1560 |
| aataacactc tactcttact tgttggaaaa aaatagtatt agcaaccacg catatgcaaa | 1620 |
| ttttaatgca gtaataataa gagatggatc gatcgttttc cagctcttgt atatgtgact | 1680 |
| ggccctgctt tatgtgtgta gtgttaattt cagctttagc agtacgtgat tagtgatgga | 1740 |
| caataattgt cgcagacgta tctatcaatt gctcctgttg tgtgatgctt taactgttgg | 1800 |
| aatcaaagtt gcgttgcctt tgttgttatg aggaggaata tatatgttgg ggcaggaaaa | 1860 |
| gaatggagga gagatcgttc tccatatcct tatcatcggc ctcgtcactg ctcgcagttt | 1920 |
| aactttttgg tgatgcgagc gatggtcagc catatatata ctcccatgct gcatgctagt | 1980 |
| aatcaatata cgccttgtaa aagtaaacga tcgtctagta attgcaatat ataggggta | 2040 |
| gccattgaca gagatctaca tagatagagg gggaacaaga attgacactc cacagatgct | 2100 |
| ccactcattc accttcacta atttatatct tttgatgttt gatcgatcga tcgatccgtc | 2160 |
| cgtcggtgtc tcgacgaata aaaactgcaa atcgaactgt atgtatataa tatagcgtcg | 2220 |
| taaattaaat taaattaaat cgaactgaat actacatgtc gaagcaagaa ttagttcaac | 2280 |
| taaaagattt agttttttccg gttgcaatat ttgtgaaatt aattgaagaa attaagaaga | 2340 |
| aaactggaga gatatatata tggatgagac aaaatgagat aagacgcatg gtggtccctc | 2400 |
| ggatgatgtc gtccgttcct tatttccatt ccatggcagc tgctatcgct atctagtgcg | 2460 |
| cgcggcatct ccaatcccat ccattctagt ggtcgatcta gctactactg agtattgttt | 2520 |
| tttcttcttt ttactactgt tgattattct gcaactgcag ttagatgctt gctactccta | 2580 |
| catcgatctc tctcgcgcgg gcgtatgcat tgcattcact actgatgatc cgtgggtgta | 2640 |
| gtgtgggtgg ctataaatag ggcagggtgc ggttgccatt gctcctcagg ccaggatcc | 2699 |

<210> SEQ ID NO 3
<211> LENGTH: 4077
<212> TYPE: DNA
<213> ORGANISM: Oryza sativa L.cv.Nipponbare

<400> SEQUENCE: 3

| | |
|---|---|
| gaattctcga tcgatcgagc aacgaacagc atatggctca cagcggcttc tccggcagcc | 60 |
| tgacgtcgcc gaggttcgac ctcgccgtcg acatgggcca tcccttcctc aaccgcaccg | 120 |
| tcgacggctt cctcaagatt ggcgctgtac ataatacatc tctctctctc tctctctctc | 180 |
| tctctctctc tcaattaatc tctgcatctt atgtattatc ttttatttaa tcgaataata | 240 |

-continued

| | |
|---|---|
| atcgatgcag gttggggctt gcaaggtcgc tgccgaagag accttcgagt gccttcacag | 300 |
| aggtctcaac tttacttcat ctgctgcata tataatttcc ctatcatcgt gttcatttct | 360 |
| ctctcatcca aaagggacaa agacacacca gagacaacat gaatctctcc tgtggccatc | 420 |
| atttctaccc accatatttg tttttaatgt tgtcactctc cttctctatt aatacataag | 480 |
| cttttacccc ttttcaaata tataattcac ccactgaata atgcactttc agagttagtg | 540 |
| ctccatgcta ttttgacttt tgacctgttt ctttctgcag gggacgtctc aaagcacaaa | 600 |
| gttgagagtg cagtaagtat atataaatac actcacattt ccatagcttt gcatccgtta | 660 |
| ttccattttc tctctatctg ctgttccatc aaggacagtt tcttcagaaa tgaagttact | 720 |
| gtttccccac ctaatactgc tatactcctg ctgatcttgc gctcctgaat ttatatgtat | 780 |
| gcagctcaag aaaatttgca aggaaggcgc atattggggt ataattaaat aatcaactca | 840 |
| tctgcatata taatctccta cttcctccgt ttcacaatgt aagactttt agcattgccc | 900 |
| atattcattt agatgttaat gaatctagac atatgtatgt gtttagattc attaacgtct | 960 |
| atatgtatat gagcaatgct agaaagtctt acattgtgaa acggagggag tacttgattt | 1020 |
| tctattaact cagctttgct caaaactaac aaaatactac tgtcaacgta ctcaagcgca | 1080 |
| tgtgttgtat ttttgttaat ctaacaatgg aagaaacaca tattcaggta ctattgcggg | 1140 |
| tgtatatgtg ggcatggagt atggaatcga agaatccgt ggtcacaggg actaggtaat | 1200 |
| atacgcatat ggtgtttgat taatttggtc ggagtaaatc tcaaaatact tggaccaaac | 1260 |
| tatcgcaaag ctacaaattt aatgttgtgc atcacaaaac tataaattta atgacttgta | 1320 |
| ccacgaaact acagattttg taatgaattt atcaaagaac tacagatttt aaagtttaaa | 1380 |
| tcaatagcct gttgtttttc tgaaagttac aaaagctaca gttttataat aaaattgatg | 1440 |
| ttaaatttgt agtttggtga taatttagta ctaaatctgg cagacgcact cttaaatata | 1500 |
| tagttttgtg atagtttgat taaagcatct gtagttttgg aaaatgtact catctgttca | 1560 |
| tgaatatata ctggctgctg tctgtgcagt gtgcacgatc gatctggatg ttaacttgca | 1620 |
| tttccttggg atgtgtgtgt atgcaattga gcagaagaac gcgatggttg gaggcgccgt | 1680 |
| aacaggagca ctggtgtctg cggcgagcaa cagccacagg cagaacgtgg tgaagaacgc | 1740 |
| catcactggg ggagccatcg caaccgctgc agagttcctc aattacctta cctgaagtct | 1800 |
| gcatactact tgttgttgat ctgtgccccc aagaagaata acactctact cttacttgtt | 1860 |
| ggaaaaaaat agtattagca accacgcata tgcaaatttt aatgcagtaa taataagaga | 1920 |
| tggatcgatc gttttccagc tcttgtatat gtgactggcc ctgctttatg tgtgtagtgt | 1980 |
| taatttcagc tttagcagta cgtgattagt gatggacaat aattgtcgca gacgtatcta | 2040 |
| tcaattgctc ctgttgtgtg atgctttaac tgttggaatc aaagttgcgt tgcctttgtt | 2100 |
| gttatgagga ggaatatata tgttggggca ggaaaagaat ggaggagaga tcgttctcca | 2160 |
| tatccttatc atcggcctcg tcactgctcg cagtttaact ttttggtgat gcgagcgatg | 2220 |
| gtcagccata tatatactcc catgctgcat gctagtaatc aatatacgcc ttgtaaaagt | 2280 |
| aaacgatcgt ctagtaattg caatatcata ggggtagcca ttgacagaga tctacataga | 2340 |
| tagaggggga acaagaattg acactccaca gatgctccac tcattcacct ttactaattt | 2400 |
| atatcttttg atgtttgatc gatcgatcga tccgtccgtc ggtgtctcga cgaataaaaa | 2460 |
| ctgcaaatcg aactgtatgt atataatata gcgtcgtaaa ttaaattaaa ttaaatcgaa | 2520 |
| ctgaatacta catgtcgaag caagaattag ttcaactaaa agatttagtt tttccggttg | 2580 |
| caatatttgt gaaattaatt gaagaaatta agaagaaaac tggagagata tatatatgga | 2640 |

```
tgagacaaaa tgagataaga cgcatggtgg tccctcggat gatgtcgtcc gttccttatt    2700
tccattccat ggcagctgct atcgctatct agtgcgcgcg gcatctccaa tcccatccat    2760
tctagtggtc gatctagcta ctactgagta ttgttttttc ttcttttac tactgttgat    2820 tattctgcaa ctgcagttag atgcttgcta ctcctacatc gatctctctc gcgcgggcgt    2880
atgcattgca ttcactactg atgatccgtg gtgtagtgt gggtggctat aaatagggca    2940
gggtgcggtt gccattgctc ctcaggccag caactgagaa gctccataca agtaagcagc    3000
agctagttgc cgacaaggcc agagaaggaa gaagaagctc tcatcatcat caccatgtcg    3060
tgctgcggtg gcaactgcgg atgcggctcc agctgccagt gcggcaacgg ctgcggcggg    3120
tacgtatatt acatgcagat cgatcgatcg atgcaattca aacttgacga tcgatatatg    3180
cagatgcaag tactctgagg tggaacccac gaccacgacc accttccttg ccgatgcaac    3240
caacaagggg tatgtacgta tacccatgct tgattaatta tacatactcc gatcgataga    3300
ttttatataa gtatgaacac tatatatcca ttacatgggc aatgcatgat cgattgcagg    3360
tctggtgctg cttccggagg atcagagatg ggggcggaga acggcagctg cggctgcaac    3420
acctgcaagt gcggcaccag ctgcggctgc tcctgctgca actgcaacta aagaaaactt    3480
atctccatcc aattcatcac ctgatcaacg agctaccagt accactacat atgccatgta    3540
ctagctacct agcttgcatg caagtcctta atttgctgct agctagctag ctacctacct    3600
tagcgtctca tgtatgtcat gttgccgcct ggccctaaa taaaattcct tacttaatcg    3660
caaaatctta tttatataca ttttctttgt cttaactata tactatactc ctgctgcatg    3720
caagcagagg ctatatatga tcgagagagt acgtaattct aatcctacca tcttattaat    3780
tcatattaac ttggctgctt atatacttct gtaacctcga tctcaaaaaa aagtgaaaca    3840
agctgagcct aatattgaga aactgaatta ctacacgcaa aagttcagcg ccagacaggt    3900
attgatgatg catatcctct gcggtataac ggttgctact gcctctgcag tattacaggg    3960
gatccctgtt ggacaggcaa agggaatgca ccctgaccat tgctgcttgt gctacctccc    4020
tggagcaaag gataatttat agaggatgct tgtatgagtt gaatcatata ggaattc      4077
```

<210> SEQ ID NO 4
<211> LENGTH: 30
<212> TYPE: DNA
<213> ORGANISM: Artificial Sequence
<220> FEATURE:
<223> OTHER INFORMATION: PCR primer used to obtain PCR products Mt pro1
      and Mt pro2, and also used to amplify the part between the
      promoter gene and the GUS gene, using a genomic DNA extracted from
      the transformed tobacco as a template

<400> SEQUENCE: 4
ttttgtcgac cttcgagtgc cttcacagag                                    30

<210> SEQ ID NO 5
<211> LENGTH: 31
<212> TYPE: DNA
<213> ORGANISM: Artificial Sequence
<220> FEATURE:
<223> OTHER INFORMATION: PCR primer used to obtain PCR product Mt pro1

<400> SEQUENCE: 5
ttttggatcc ggtgatgatg atgagagctt c                                  31

<210> SEQ ID NO 6
<211> LENGTH: 30

```
-continued

<212> TYPE: DNA
<213> ORGANISM: Artificial Sequence
<220> FEATURE:
<223> OTHER INFORMATION: PCR primer used to obtain PCR product Mt pro2

<400> SEQUENCE: 6
ttttggatcc tggcctgagg agcaatggca                              30

<210> SEQ ID NO 7
<211> LENGTH: 22
<212> TYPE: DNA
<213> ORGANISM: Artificial Sequence
<220> FEATURE:
<223> OTHER INFORMATION: Primer used to amplify the part between the
      promoter gene and the GUS gene, using a genomic DNA extracted
      from the transformed tobacco as a template

<400> SEQUENCE: 7
cccggctttc ttgtaacgcg ct                                     22
```

What is claimed is:

1. A DNA fragment comprising a DNA sequence shown by SEQ ID NO: 1, or a DNA sequence the complement thereof which hybridizes to SEQ ID NO: 1 under stringent hybridization conditions of 5×SSC, 5×Denhardt's reagent, and 0.5% SDS at 65° C., wherein the DNA sequence has a function to control expression of structural gene which can be expressed in plants.

2. An expression vector comprising the DNA fragment according to claim 1.

3. An expression vector comprising the DNA fragment according to claim 1 and an exogenous gene linked thereto.

4. A transformed plant cell comprising the expression vector of claim 3.

5. A transformed plant comprising the transformed plant cell according to claim 4.

6. A seed comprising the transformed plant cell according to claim 4.

7. A DNA fragment comprising a DNA sequence shown by SEQ ID NO: 2, or a DNA sequence the complement thereof which hybridizes to SEQ ID NO: 2 under stringent hybridization conditions of 5×SSC, 5×Denhardt's reagent, and 0.5% SDS at 65° C., wherein the DNA sequence has a function to control expression of structural gene which can be expressed in plants.

8. An expression vector comprising the DNA fragment according to claim 7.

9. An expression vector comprising the DNA fragment according to claim 7 and an exogenous gene linked thereto.

10. A transformed plant cell comprising the expression vector of claim 9.

11. A transformed plant comprising the transformed plant cell according to claim 10.

12. A seed comprising the transformed plant cell according to claim 10.

13. A DNA fragment comprising a DNA sequence shown by SEQ ID NO: 3, or a DNA sequence the complement thereof which hybridizes to SEQ ID NO: 3 under stringent hybridization conditions of 5×SSC, 5×Denhardt's reagent, and 0.5% SDS at 65° C., wherein the DNA sequence has a function to control expression of structural gene which can be expressed in plants.

14. A DNA fragment comprising a DNA sequence selected from the group consisting of: SEQ ID NO: 1, SEQ ID NO: 2 and SEQ ID NO:3, wherein said DNA sequence has a function to control expression of structural gene which can be expressed in plants.

* * * * *

UNITED STATES PATENT AND TRADEMARK OFFICE
CERTIFICATE OF CORRECTION

PATENT NO. : 6,759,526 B2
DATED : July 6, 2004
INVENTOR(S) : Uchimiya et al.

It is certified that error appears in the above-identified patent and that said Letters Patent is hereby corrected as shown below:

<u>Title page,</u>
Item [30], Foreign Application Priority Data, please change
"December 2, 1999    (JP)......................11-343624" to
-- December 2, 1999    (JP)......................11-343625 --

Signed and Sealed this

Seventh Day of December, 2004

JON W. DUDAS
*Director of the United States Patent and Trademark Office*